(12) United States Patent
Dinan et al.

(10) Patent No.: US 7,098,232 B1
(45) Date of Patent: Aug. 29, 2006

(54) TREATMENT AND PREVENTION OF GASTROINTESTINAL DISEASE USING ANTAGONISTS OF PARTIAL AGONISTS OF 5HT1A RECEPTORS

(75) Inventors: Timothy G. Dinan, Co. Cork (IE); Patrick W. N. Keeling, Dublin (IE)

(73) Assignee: Athpharma Limited, Roscommon (IE)

( * ) Notice: Subject to any disclaimer, the term of this patent is extended or adjusted under 35 U.S.C. 154(b) by 0 days.

(21) Appl. No.: 09/687,384

(22) Filed: Oct. 13, 2000

Related U.S. Application Data

(60) Provisional application No. 60/161,117, filed on Oct. 22, 1999.

(51) Int. Cl.
*A61K 31/405* (2006.01)

(52) U.S. Cl. ...................................... 514/415; 514/469
(58) Field of Classification Search ................. 514/415, 514/651
See application file for complete search history.

(56) References Cited

U.S. PATENT DOCUMENTS

| | | | | | |
|---|---|---|---|---|---|
| 5,403,848 | A | * | 4/1995 | Dinan et al. | 514/325 |
| 5,859,065 | A | * | 1/1999 | Brandes | 514/651 |
| 6,159,979 | A | * | 12/2000 | Gaster et al. | 514/252.12 |

FOREIGN PATENT DOCUMENTS

RO    RO 92436    9/1987

OTHER PUBLICATIONS

Fisher, R. S. et al., "Management of Nonulcer Dyspepsia," *The New England Journal of Medicine*, vol. 339, pp. 1376–1381, 1998.
Brown, C. et a., "Dyspepsia in General Practice," *BMJ*, vol. 200, pp. 829–830, 1990.
Nyréen, O. et al., "Excess Sick–Listing in Nonulcer Dyspepsia, " *Journal of Clinical Gastroenterology*, vol. 8, pp. 339–345, 1986.
Thakore, J. H. et al., "Treating Depression with SPecific Serotonergic Acting Agents," *Journal of Serotonin Research*, vol. 3, pp. 145–160, 1996.
Talley, N. J. et al., "Dyspepsia and Dyspepsia Subgroups: A Population–Based Study," *Gastroenterology*, vol. 102, pp. 1259–1268, 1992.
Talley, N. J. et al., "Non–Ulcer Dyspepsia: Potential Causes and Pathophysiology," *Annals of Internal Medicine*,vol. 108, pp. 865–879, 1988.
Dotevall, G., "Psychosomatic Gastroenterlogy Today and Some Ideas for Tomorrow," *Gastroenterol International*, vol. 2, pp. 96–100, 1989.
Gershon, M. D., "The Nervous System of the Gut," *Gastroenterology*, vol. 80, pp. 1571–1594, 1981.
Baumgarten, H. G., "Neuroanatomy and Neurophysiology of Central Serotonergic Systems," *Journal of Serotonin Research*, vol. 3, pp. 171–179, 1994.
Lundgren, O. et al., "Enteric Nervous System: I. Physiology and Pathophysiology of the Intestinal Tract," *Digestive Diseases and Sciences*, vol. 34, pp. 264–283, 1989.
Rowland, N. et al. "Inhibition of Gastric Emptying by Peripheral and Central Fenfluramine in Rats: Correlation with Anorexia," *Life Sciences*, vol. 34, pp. 2495–2499, 1984.
Talley, N. J. et al., "Functional Dyspepsia: A Classification with Guidelines for Diagnosis and Management," Gastoenterology International, vol. 4, pp. 145–160, 1991.
Dinan, T. G. et al., "Serotonin Sypersensitivity: The Pathophysiologic Basis of Non–Ulcer Dyspepsia?" *Scandinavian Journal of Gastroenterology*, vol. 25, pp. 541–544, 1990.
Chua, A. et al., "Central Serotonin Receptors and Delayed Gastric Emptying in Non–Ulcer Dyspepsia," BMJ, vol. 305, pp. 280–282, 1992.
Lamberts, S. W. J., "Regulation of Prolactin Secretion at the Level of the Lactotroph," *Physiological Reviews*vol. 70, pp. 279–318, 1990.
Meltzer, H. Y. et al., "Effects of Buspirone on Plasma Prolactin and Cortisol Levels in Major Depressed and Normal Subjects," *Society of Biological Psychiatry*, vol. 35, pp. 316–323, 1994.
Corradetti, R. et al., "Antagonist Properties of (−)–pindolol and WAY 100635 at Somatodendritic and Postsynaptic 5–HT$_{1A}$ Receptors in the Rat Brain," *British Journal of Pharmacology*, vol. 123, pp. 449–462, 1998.

* cited by examiner

*Primary Examiner*—Christopher S. F. Low
*Assistant Examiner*—Donna Jagoe
(74) *Attorney, Agent, or Firm*—Finnegan, Henderson, Farabow, Garrett & Dunner, L.L.P.

(57) ABSTRACT

The present invention provides a method for preventing and treating gastrointestinal diseases such as dyspepsia, irritable bowel disease and chemotherapy-associated nausea by administering an antagonist or partial agonist of 5HT1a receptors.

4 Claims, No Drawings

TREATMENT AND PREVENTION OF GASTROINTESTINAL DISEASE USING ANTAGONISTS OF PARTIAL AGONISTS OF 5HT1A RECEPTORS

This application claims the priority of Provisional Application No. 60/161,117 filed Oct. 22, 1999.

FIELD OF THE INVENTION

The present invention provides a method for preventing and treating gastrointestinal diseases such as dyspepsia, irritable bowel disease and chemotherapy-associated nausea by administering an antagonist or partial agonist of 5HT1a receptors.

BACKGROUND OF THE INVENTION

Dyspepsia is a common symptom ranging in prevalence from 26% in the United States to 41% in England (1). Whilst only 1 in 4 patients seek medical help (2) the condition results in significant health care costs (3) and an organic cause is found in only 40% of patients. The Rome criteria for diagnosing idiopathic or nonulcer dyspepsia (NUD) were put forward in 1991 and consist of chronic or recurrent upper abdominal pain or discomfort in the absence of obvious pathology (4). The Rome group suggested subcategorising NUD into ulcer-like, reflux-like, dysmotility-like and non-specific dyspepsia. This classification has been questioned on the grounds that there is a marked overlap of symptoms and an overlap between the symptoms and those of the irritable bowel syndrome (5).

Conventional diagnosne evaluation (endoscopy, ultrasonography, 24 h ambulatory pH monitoring) does not reveal a structural or biochemical abnormality to explain NUD. Attempts at elucidating the pathophysiology of the condition have produced inconsistent findings (6) and a wide array of theories are currently put forward (7).

Serotonin (5HT) is a neurotransmitter both in the enteric nervous system (8) and in the brain (9). It plays a key role in regulating gut physiology, including peristalsis and intestinal tone (10). Animal studies have shown that intracerebroventricular injection of fenfluramine (a serotonin releasing agent) inhibits gastric emptying (11). Selective serotonin reuptake inhibitors, such as fluoxetine and sertraline, are widely used in the treatment of depression and produce a transient syndrome similar to NUD in up to 30% of patients treated (12).

Studies indicate that a central 5HT1a receptor hypersensitivity may be involved in the pathophysiology of NUD (13,14). The release of prolactin from the anterior pituitary is under dopamine inhibition and under 5HT stimulation, probably at the level of the hypothalamus (15). Buspirone is an azaspirodecanedione, which acts as a partial agonist at the 5HT1a receptor (16) and stimulates prolactin release, We have established that prolactin release following buspirone challenge is enhanced in NUD indicating 5HT1a receptor supersensitivity in this condition.

We have demonstrated this in a clinical study that extends our previous findings reported in U.S. Pat. No. 5,403,848.

A total of 109 subjects, 50 NUD patients (39 female/11 male) and 59 healthy comparison subjects (32 female/28 male) gave fully informed consent to take part in the study, which had Ethics Committee approval. The mean±SD age of the patients was 35.6±12.2 years (Range 20–62) and of the comparison group 27.2±7.6 years (Range 20–52). At 0830 h subjects had a cannula inserted in a forearm vein. Buspirone (30mg) or, matching placebo was administered orally at 0900 h (Time 0). Blood was taken at 0, 30, 60, 90, 120 and 180 min. Prolactin levels rose in all subjects challenged with buspirone. The mean±SD AUC in patients was 46±35 and in healthy subjects 24±35. A 2-way repeated measures ANOVA yields a significant group X time interaction with differences significant at 60 min (p<0.05), 90 min (p<0.01) and 120 min (p<0.05). Prolactin concentration at 90 min provided the best discrimination between the two groups.

According to the present invention, what is required to treat non-ulcerative dyspepsia is the administration of effective amounts of a substance that reduces the sensitivity of 5HT1a receptors and we have discovered that pindolol, which has affinity for 5HT1a receptors has beneficial effects in subjects suffering from non-ulcerative dyspepsia.

SUMMARY OF THE INVENTION

The present invention provides a means for prevention and treatment of gastrointestinal disease by administration of a substance that reduces the sensitivity of 5HT1a receptors. A preferred means is the administration of RS pindolol or a salt thereof. An especially preferred means is the administration of S(−) pindolol or a salt thereof.

DETAILED DESCRIPTION OF THE INVENTION

As noted earlier, this invention can use any substance that is an antagonist or a partial agonist of 5HT1a receptors such that the sensitivity of 5HT1a receptors described above is reduced.

Pindolol is a beta adrenergic antagonist, used in the treatment of hypertension and angina. It also has affinity for 5HT1a receptors of a similar magnitude as its affinity for beta adrenergic receptors. Until now, no therapeutic applications of this phenomenon have been discovered. Pindolol is used therapeutically in hypertension and angina as the racemic substance, RS pindolol. Most or all of the pharmacological effects of pindolol are possessed by the isomer S(−) pindolol. The present invention utilizes pindolol to reduce the sensitivity of 5HT1a receptors and as a result to provide the means for prevention and treatment certain gastrointestinal diseases, including non-ulcerative dyspepsia. A preferred embodiment of the invention is the isomer S(−) pindolol or salts thereof. Another method utilizes the administration of cyproheptadine, described in U.S. Pat. Nos. 5,324,738 and 5,403,848. The latter also describes a method for diagnosis of non-ulcerative dyspepsia by measuring the responsiveness of 5HT1a receptors. RS pindolol has an advantage over cyproheptadine of greater selectivity for the 5HT1a receptor and S(−) pindolol has further advantages of greater potency and specificity. The invention is likely to be effective in various presentations of gastrointestinal disease in which there is altered sensitivity of 5HT1a receptors. We have specific demonstration of the role of 5HT1a receptors in non-ulcerative dyspepsia, but there is likely to be also benefit in certain cases of irritable bowel syndrome, especially that occurring in the upper intestinal region and in certain cases of motility disorders (including nausea) caused by cancer chemotherapy.

Various pharmaceutical presentations are possible, including (but not limited to) tablets, capsules, oral solutions and suspensions and parenteral solutions. Included are also pharmaceutical formulations for oral use in which the active substance is released in a controlled and slower fashion such that the treatment may be administered less frequently.

The usual doses of RS pindolol and S(−) pindolol will be in the range of 2.5 mg to 50 mg daily in single or divided doses, depending upon the therapeutic response and the pharmaceutical form. The usual doses of S(−) pindolol will be lesser than those of RS pindolol since the former will be more potent because it is responsible for most or all of the pharmacological effects.

The invention is intended for the treatment of mammals, including humans. The ability of the invention to treat gastrointestinal disease has been demonstrated in a clinical study.

EXAMPLE

Eleven patients suffering from non-ulcerative dyspepsia were recruited to a clinical study and gave informed consent. All were treated with pindolol 2.5 mg three times daily. Seven of the 11 patients show ed a significant improvement in symptoms within 1 week of commencing treatment. A further patient improved in the second week. Their responses were quantified using a standard rating scale (GSRS scores). The results demonstrated a substantial improvement with a reduction in average symptom severity of approximately 68% in three weeks, with the greatest improvement observed within one week.

TABLE 1

Mean symptom score (average of 11 patients)

| Week | Mean GSRS Score |
|------|-----------------|
| 0 | 9 |
| 1 | 4.2 |
| 2 | 3.5 |
| 3 | 2.9 |

REFERENCES TO PREVIOUS PATENTS

T. G. Dinan and P. W. N. Keeling U.S. Pat. No. 5,324,783
T. G. Dinan and P. W. N. Keeling U.S. Pat. No. 5,403,848

OTHER REFERENCES

1. Fisher RS, Parkinan HP. Management of nonulcer dyspepsia. N Engl J Med 1998;339:13⁻6–81
2. Brown C, Rees EWE. Dyspepsia in general practice. BMJ 1990;300:829–30.
3. Nyren O, Adaini HO, Gustavsson S, Loof L. Excess sick-listing in nonulcer dyspepsia. J Clin Gastroenterol 1986;8:339–45.
4. Talley NJ, ColinJones D, Koch KI, Koch M, Nyren O, Stranghellini V. Functional dyspepsia: a classification with guidelines of diagnosis and management Gastroenterol Int 1991;4:145–60.
5. Talley NJ, Zinseister AR, Schleck CD, Melton LJ. Dyspepsia and dyspepsia subgroupings: a population-based study, Gastroenterology 1992;102:1259–68.
6. Talley NJ, Philips SF. Non-ulcer dyspepsia; potential causes and pathophysiology. Ann Intern Med 1988;108:865–79.
7. Dotevall G. Psychosomatic gastroenterology today and some ideas for tomorrow. Gastroenterol Int 1989;2:96–100.
8. Gershon MD. Erde SM. The nervous system of the gut. Gastroenterology 1981;80;1571–94.
9. Baumagarten HG, Grozdanovic Z. Neuroanatomy and neurophysiology of central serotonergic systems. J Serotonin Res 1994;1:171–81.
10. Lundgren O. Svanvik J, Jivegard L. Enteric nervous system: 1. Physiology and pathophysiology of the intestinal tract. Digest Dis Sci 1989;34:264–83.
11. Rowland, N, Carlton J. Inhibition of gastric emptying by peripheral and central fenfluramine in rats: correlation with anorexia Life Sci 1984;34:2495–9.
12. Thakore JH. Berti C, Dinan TG. Treating depression with specific serotonergic acting agents. J Serotonin Res 1996;3:145–160.
13. Dinan TG, Yatham LN, Barry S, Chua A, Keeling PWN. Serotonin supersensitivity: the pathophysiologic basis of non-ulcer dyspepsia? A preliminary report of buspirone/prolactin responses. Scand J Gastroenterol 1990;25:541–44.
14. Chua A, Keating J, Hamilton D, Keeling PWN, Dinan TG. Central serotonin receptors and delayed gastric emptying in in-ulcer dyspepsia. BMJ 1992;305:280–2.
15. Lamberts SWJ, Macleod RM. Regulation of prolactin secretion at the level of the lactrotroph. Physiol Rev. 1990;70:279–318.
16. Meltzer HY, Maes M. Effects of buspirone on plasma prolactin and cortisol levels in major depressed and normal subjects. Biol Psychiat. 1994;35:316–323.

What is claimed is:

1. A method for treating at least one gastrointestinal disease comprising administering a composition consisting essentially of an effective amount of amount of S(-) pindolol, or a salt thereof as the sole active agent, to a subject in need of said treatment, wherein the effective amount of S(-) pindolol, or a salt thereof, ranges from greater than 3 mg/per day to about 50 mg/per day in a single or divided dose, wherein the at least one gastrointestinal disease is chosen from non-ulcerative dyspepsia, irritable bowel syndrome, cancer chemotherapy-associated disorders of motility, and combinations thereof.

2. The method according to claim 1, wherein an effective amount of S(-) pindolo, or a salt thereof, is administered in a pharmaceutical dosage form that permits rapid release of the S(-) pindolol.

3. The method according to claim 1, wherein an which effective amount of S(-) pindolol, or a salt thereof, is administered in a pharmaceutical dosage form that releases the S(-) pindolol in a slow or controlled fashion.

4. The method according to claim 1, wherein the cancer chemotherapy-associated disorders of motility is nausea.

* * * * *

UNITED STATES PATENT AND TRADEMARK OFFICE
CERTIFICATE OF CORRECTION

PATENT NO. : 7,098,232 B1  Page 1 of 1
APPLICATION NO. : 09/687384
DATED : August 29, 2006
INVENTOR(S) : Dinan et al.

It is certified that error appears in the above-identified patent and that said Letters Patent is hereby corrected as shown below:

On the title page, item (54), line 3, "OF PARTIAL" should read --OR PARTIAL--.

In claim 1, column 4, line 36, delete the second occurrence of "amount of".

In claim 2, column 4, line 46, "S(-) pindolo," should read --S(-) pindolol,--.

In claim 3, column 4, lines 50-51, "an which effective" should read --an effective--.

In claim 3, column 4, line 51, "of S(-) pindolol," should read --of the S(-) pindolol,--.

In claim 4, column 4, line 55, "disorders" should read --disorder--.

Signed and Sealed this

Nineteenth Day of December, 2006

JON W. DUDAS
*Director of the United States Patent and Trademark Office*